United States Patent [19]

Müller et al.

[11] 4,405,500
[45] Sep. 20, 1983

[54] HALOGEN COMPOUND PROMOTED $Al_2O_3$ AND/OR $SiO_2$ FOR THE PREPARATION OF ISOALKENES

[75] Inventors: Hans J. Müller, Leverkusen; Helmar Hönig, Hamburg; Werner Horlitz, Dormagen, all of Fed. Rep. of Germany

[73] Assignee: EC Erdolchemie GmbH, Cologne, Fed. Rep. of Germany

[21] Appl. No.: 326,711

[22] Filed: Dec. 2, 1981

[30] Foreign Application Priority Data

Dec. 23, 1980 [DE] Fed. Rep. of Germany ....... 3048693
Apr. 29, 1981 [DE] Fed. Rep. of Germany ....... 3117053
Sep. 19, 1981 [DE] Fed. Rep. of Germany ....... 3137383

[51] Int. Cl.$^3$ .............. B01J 27/08; B01J 27/12; B01J 21/02; C07C 11/02
[52] U.S. Cl. .................................. 252/433; 252/415; 252/441; 252/442; 252/463; 585/669
[58] Field of Search ............... 252/433, 441, 442

[56] References Cited

U.S. PATENT DOCUMENTS

| | | | |
|---|---|---|---|
| 2,381,562 | 8/1945 | Stewart | 252/442 |
| 3,114,785 | 12/1963 | Hervert et al. | 252/433 |
| 3,663,453 | 5/1972 | Myers | 252/441 |
| 3,919,117 | 11/1975 | Michalko | 252/448 |
| 3,919,340 | 11/1975 | Hayes | 208/139 |
| 3,975,299 | 8/1976 | Crathorne et al. | 252/442 |
| 4,014,948 | 3/1977 | Myers | 208/111 |
| 4,216,122 | 8/1980 | Michalko | 252/448 |
| 4,250,058 | 2/1981 | Michalko | 252/448 |

FOREIGN PATENT DOCUMENTS

| | | |
|---|---|---|
| 32543 | 7/1981 | European Pat. Off. . |
| 869061 | 3/1953 | Fed. Rep. of Germany . |
| 1518580 | 2/1969 | Fed. Rep. of Germany . |
| 1518584 | 3/1971 | Fed. Rep. of Germany . |
| 1518595 | 3/1971 | Fed. Rep. of Germany . |
| 482185 | 12/1975 | U.S.S.R. ................ 585/669 |

OTHER PUBLICATIONS

Revised Form of Mendeleev's Periodic Chart.

*Primary Examiner*—P. E. Konopka
*Attorney, Agent, or Firm*—Sprung, Horn, Kramer & Woods

[57] ABSTRACT n-Alkenes can be converted catalytically into isoalkenes, when a mixture containing at least one n-alkene and hydrogen is brought into contact at a temperature of 400° to 600° C. and a residence time of 0.2 to 20 seconds with an $Al_2O_3$ or $SiO_2$ catalyst which is specifically activated and is promoted with halogen compounds of elements of the third to fifth main groups and second to eighth sub-groups of the periodic system and/or hydrohalic acids. The specific activation comprises calcining, before the promotion process, an aluminum hydroxide or aluminum oxide hydrate or a silica gel having a content of volatile ammonium salts to give $Al_2O_3$ or $SiO_2$, with expulsion of these volatile ammonium salts. For the conversion of the n-alkenes, the catalyst can be employed in a fixed or a mobilized catalyst bed. In cases where the catalyst is used in a mobilized catalyst bed it can be passed, by continuous or discontinuous removal of a portion of it, to a separate regeneration process and following regeneration can be reintroduced into the mobilized catalyst bed.

19 Claims, 2 Drawing Figures

HALOGEN COMPOUND PROMOTED AL₂O₃ AND/OR SIO₂ FOR THE PREPARATION OF ISOALKENES

BACKGROUND OF THE INVENTION

1. Field of the Invention

The invention relates to a process for the preparation of isoalkenes by catalytic conversion of n-alkenes, a catalyst which is suitable for this conversion, and a process for the preparation of such a catalyst.

2. Discussion of Prior Art

It is generally known that n-paraffins with, for example, 4 to 7 C atoms can be converted to the corresponding isomeric paraffins by using suitable acid catalysts in the temperature range of from 100° to 250° C. Examples of this process are the numerous isomerization processes used in the petrochemical and mineral oil industries for increasing the octane number of light, paraffinic mineral oil fractions. Furthermore, it is known that, in contrast to this, olefins of the same number of carbon atoms cannot be converted to the corresponding isoolefins or can only be converted to the corresponding isoolefins under difficult conditions, for example at very high temperatures, and with poor yield. The attempts hitherto described in the literature for the direct isomerisation of the skeleton of e.g. n-butene to give isobutene or e.g. of n-pentene to give isopentenes at catalysts arranged in a fixed bed are characterized by only initially high yields and selectivities, which diminish and deteriorate considerably after a short period of operation, often after only a few hours. The deterioration in the yields and selectivities is generally attributed to the loss of actively effective catalyst surface or to the loss of active centers. Owing to this high coking rates, formation of oligomers and cracking reactions are observed.

Thus, in U.S. Pat. No. 3,531,542, a process is described for obtaining isobutene from n-butene, in which an Al₂O₃ catalyst arranged in a fixed bed is employed in a number of stages. In U.S. Pat. No. 3,663,453 the same conversion is conducted also in a fixed bed, with a catalyst consisting of zirconium oxide and an Al₂O₃/ZrOCl₂ catalyst. The catalytic isomerization of olefinic hydrocarbons in a fixed bed is also described in U.S. Pat. No. 2,568,964. It is reported that carbon deposits form on the catalyst material during the isomerization process, which reduce the activity and necessitate periodic regeneration of the catalyst. It is stated that the catalyst regains its full activity after regeneration, but one disadvantage which at least remains is that the isomerization process itself has to be interrupted during the period of regeneration.

The following combination of substances may be mentioned in the place of other alkenes, using butenes as examples:

Distillation fractions which contain n-butene, optionally mixed with isobutene, isobutane and n-butane, are often produced in petrochemical plants or in refineries, as, for example, after the separation of 1,3-butadiene from a C₄-cut or in the cracking of waxy distillates. The optionally present isobutene in such distillation fractions is reacted, above all, in catalytic reactions, for example with methanol to give methyl-tert.-butyl ether, which is separated off by distillation from the residual C₄-cut, and can be used for improving the antiknocking properties of gasoline or as a solvent. A further catalytic reaction of isobutene in such mixtures is the oligomerization in presence of acid catalysts to give, for example, C₈-, C₁₂- or C₁₆-oligomers of the isobutene, which can likewise be separated off by distillation. In both cases, a mixture of n-butenes, n-butane and isobutane remains as a residual product, which can only be put to a minor use, for example as fuel gas, in most cases.

It is therefore desirable again to prepare a mixture containing isobutene from the n-butene/n-butane/isobutane mixture, which remains as a residual product from the abovementioned reactions, by a catalytic conversion, and this isobutene-containing mixture can again be subjected to reactions which are described above in the form of examples.

SUMMARY OF INVENTION

A process for the preparation of isoalkenes by catalytic conversion of n-alkenes has now been found, which is characterized in that a mixture containing at least an n-alkene, hydrogen and optionally inert gases is brought into contact, at a temperature of 400° to 600° C. and a residence time of 0.2 to 20 seconds, with an Al₂O₃ and/or SiO₂ catalyst which is specifically activated and is promoted with halogen compounds of elements of the third to fifth main groups and second to eighth sub-groups of the periodic system (Mendeleev) and/or hydrohalic acids, and the specific activation comprises calcining, before the promotion process, an aluminum hydroxide and/or aluminum oxide hydrate and/or silica gel having a content of volatile ammonium salts, to give Al₂O₃ and/or SiO₂ with expulsion of the volatile ammonium salts.

The mixture to be employed in the process according to the invention contains at least one-alkene containing for example 4–8, preferably 4–5, and particularly preferably 4 carbon atoms and having a terminal or internal double bond. In the case of butene it can therefore be n-but-1-ene, n-but-2-ene or a mixture of any desired composition of these two compounds. Other n-alkenes which can be used according to the invention are for example: n-pent-1-ene, n-pentene-2, n-hex-1-ene, n-hexene-2, n-hexene-3, n-hept-1-ene, n-heptene-2 or -3 and n-oct-1-ene, -2-ene, -3-ene or -4-ene. However, these n-alkenes, or one of them, can also be accompanied by other hydrocarbons. These hydrocarbons include, primarily, those with the same number of C-atoms, e.g. in the case of the butenes such as n-butane and isobutane. Likewise, the n-alkenes which can be employed according to the invention can already contain small quantities of isoalkene, in addition to the substances mentioned. Such mixtures result from the combination of material and processes which is desired in a petrochemical plant, e.g. after the removal of other valuable compounds, such as aromatics, isoalkenes or diolefines, as is to be illustrated in the case of the C₄-hydrocarbons by the following example:

After the separation of the butadiene from a C₄-cut obtained from the thermal cracking according to one of the known processes, a C₄-mixture, containing isobutene, of the following composition remains: 35 to 45% by weight of isobutene, 30 to 50% by weight of n-butenes, 8 to 15% by weight of n-butane and 4 to 6% by weight of isobutane. After the removal of the isobutene to yield its oligomers, a residual C₄-hydrocarbon mixture with about the following composition remains: 0 to 2% by weight of isobutene, 60 to 80% by weight of n-butenes, 10 to 30% by weight of n-butane and 5 to 10% by weight of isobutane. This residual C₄-mixture which remains can be employed according to the invention.

Small contents, for example up to 10% by weight in each case, of not cleanly separated portions of the neighbouring $C_3$-hydrocarbon fraction and the $C_5$-hydrocarbon fraction in the case of n-butenes or of the other respective neighbouring fractions in the case of alkenes having more than 4 carbon atoms are also non-critical for the process according to the invention.

The mixture to be employed in the process according to the invention is characterized, furthermore, by a content of hydrogen. In general, this hydrogen is added to the n-alkene or the n-alkenes, or to a mixture containing these, before entry into the reactor filled with catalyst. In this context, a quantity of from 0.01 to 15 parts by volume, preferably 0.1 to 10 parts by volume, particularly preferably 0.5 to 5 parts by volume of hydrogen per 1 part by volume of the total amount of hydrocarbons in the starting product may be mentioned as an example. In the case in which the hydrocarbon mixture to be employed, which contains n-alkenes, already contains hydrogen from a down-stream refinery process in the order of magnitude mentioned, the addition of further hydrogen can, of course, be omitted.

Pure or industrial hydrogen can be added as the hydrogen. Industrial hydrogen can contain, for example, small quantities of hydrocarbons, such as methane or ethane, or inert gases, such as nitrogen, carbon dioxide or noble gases. The content of such substances in industrial hydrogen is calculated on the basis of the starting quantity of hydrogen, but is otherwise completely non-critical. 0.1 to 20% by volume may be mentioned as an example of the content of such substances in industrial hydrogen. The hydrogen separated off from the mixture produced in the process according to the invention can also be used again as an admixture for the starting product.

Furthermore, the inert gases, such as steam, nitrogen, carbon dioxide or argon, can be added to the mixture to be employed according to the invention, which contains at least one n-alkene and hydrogen. Such inert substances have already been mentioned, in part, as possible accompanying materials of industrial hydrogen. Among these inert substances, the addition of steam is preferred. Such inert substances can be added in a wide range of variation, for example 1 to 50% by volume, preferably 5 to 30% by volume, relative to the total mixture of n-alkenes, hydrogen and the hydrocarbons mentioned as accompanying compounds.

To improve the activity of the catalyst, halogenated hydrocarbons, such as, for example, carbon tetrachloride, chloroform, chlorinated ethanes, dichloropropane, fluorochloroethane and similar substances, can be added to the material used in the reactor. Quantities of 0.1 to 1%, discontinuously, and 1 to 100 ppm, continuously, are employed, relative to the total mixture employed.

The process according to the invention is carried out at a temperature of from 400° to 600° C., preferably 420° to 520° C., and under a pressure of from 0.5 to 10 bars, preferably 1 to 3 bars.

A residence time of from 0.2 to 20, preferably from 1 to 10, particularly preferably from 2 to 6 seconds is established in the process according to the invention. In this process, a quantity of catalyst is employed which corresponds to a quantity of from 180 to 18,000, preferably 360 to 3,600, particularly preferably 600 to 1,800 parts by volume of hourly throughput mixture per part by bulk volume of catalyst.

The stated residence time of the mixture, which has been fed in and is to be reacted, in the presence of the catalyst implies a gas velocity (GHSV=gas hourly space velocity) of about 180 to 18,000, preferably 360 to 3,600, particularly preferably 600 to 1,800 parts by volume of gas mixture per part by volume of catalyst charge per hour.

In the process according to the invention, the conversion of n-alkenes into isoalkenes, preferably n-butenes into isobutene almost up to the establishment of thermodynamic equilibrium is achieved. This equilibrium, between 400° to 500° C., is about 36 to 40% by weight in the case in which the pure system of the n-butenes and isobutene is considered. This equilibrium is frequently not achieved in the case of a single contact of the mixture to be employed according to the invention with the catalyst to be employed according to the invention. However, in particular variant of the process, the product stream leaving the catalyst bed can be divided up, and only one part is directly conveyed to the working-up process, whilst the other part is again conducted over the catalyst bed. This division of the product stream for recycling can vary within wide limits, for example between the proportions 1:9 to 9:1 of worked-up or recycled material. In this process, a high recycling rate implies a smaller throughput, relative to a constant catalyst charge and constant remaining reaction conditions, but brings a desired shift of the spectrum of components in favour of the isoalkene, e.g. of the isobutene, almost to the thermodynamic equilibrium. On the other hand, a lower recycling rate implies a higher throughput but a poorer approach to the thermodynamic equilibrium. A decision concerning the amount of the recycling rate depends, other process parameters being constant, above all on the composition of the starting hydrocarbon mixture which is available. However, with the catalysts according to the invention, the process can, in general, be operated without a high recycling rate. However, this can be optimized by simple preliminary experiments.

For example, a hydrocarbon mixture of the following composition: about 25% by weight of isobutene, about 41% by weight of n-butenes, about 25% by weight of n-butane/isobutane, about 1% by weight of $C_3$ hydrocarbons and about 8% by weight of $C_5$ and higher hydrocarbons can be obtained by the inventive process when starting from the abovementioned typical $C_4$-cut which remains after the removal of the isobutene in one of the processes mentioned, and which has the following composition: 0 to 2% by weight of isobutene, 60 to 80% by weight of n-butenes, 10 to 30% by weight of n-butane and 5 to 10% by weight of isobutane. This reaction product can, for example, by directly subjected to a further reaction for the preparation of methyl tertiary butyl ether or oligomers of isobutene, or to an extraction of the isobutene with selective solvents or with sulphuric acid. The residual gas remaining after separation of the isobutene can then again be employed in the process according to the invention.

The invention further relates to a catalyst with which the inventive conversion of n-alkenes into isoalkenes may be carried out. This catalyst comprises a specifically activated $Al_2O_3$ and/or $SiO_2$, containing 0.1 to 20% by weight, relative to the quantity of the $Al_2O_3$ and/or $SiO_2$, of a halogen compound of an element of the third to fifth main groups and second and eighth sub-groups of the periodic system (Mendeleev) and/or hydrogen halide acids, and the specific activation comprising calcining, before the promotion process, an aluminum hydroxide and/or aluminum oxide hydrate and/or silica gel with a content of volatile ammonium salts to give $Al_2O_3$ and/or $SiO_2$, with expulsion of the volatile ammonium salts.

Aluminum fluoride, aluminum chloride, aluminum bromide, boron fluoride, boron chloride, titanyl chloride, germanium chloride, germanium fluoride, tin chloride, arsenic fluoride, arsenic chloride, antimony fluoride, antimony chloride, antimony bromide, bismuth chloride, bismuth oxychloride, zinc chloride, zinc bromide, cadmium fluoride, cadmium chloride, lanthanum fluoride, lanthanum oxychloride, iron fluoride, iron chloride, iron bromide, cobalt chloride and nickel chloride may be mentioned as examples of halogen compounds of the stated elements.

Even hydrohalic acids, alone as well as in combination with the abovementioned halogen compounds, can be used as promoting agents, for example hydrogen fluoride, hydrogen chloride, hydrogen bromide, hydrogen iodide or mixtures of these compounds. The stated halogen compounds and hydrohalic acids can be employed for the promotion both as single compounds and as a mixture of several of them. Aluminum chloride, boron fluoride, antimony(III) fluoride, vanadyl chloride, titanyl chloride, bismuth oxychloride, hydrogen chloride and hydrogen bromide may be preferably mentioned as the halogen compound and/or hydrogen halide. Boron fluoride, antimony(III) fluoride and hydrogen chloride may be particularly preferably mentioned. Very particularly preferred is hydrogen chloride.

These halogen compounds and/or hydrohalic acids are used for promotion in a quantity of from 0.1 to 20% by weight, preferably 0.5 to 15% by weight, particularly preferably 1 to 10% by weight, relative to the weight of the $Al_2O_3$ and/or $SiO_2$.

The $Al_2O_3$ and/or $SiO_2$ for the catalyst according to the invention is specifically activated before promotion with the halogen compounds mentioned. This specific activation comprises the following: in the preparation of the as yet unpromoted $Al_2O_3$ and/or $SiO_2$ by calcination of aluminum hydroxide and/or aluminum oxide hydrate and/or silica gel, a volatile ammonium salt, which was absorptively bonded in the aluminum hydroxide and/or aluminum oxide hydrate and/or silica gel, is expelled, and thereby produces a particularly active structure of the calcined $Al_2O_3$ and/or $SiO_2$. The structure of the $Al_2O_3$ and/or $SiO_2$ and the promotion thereof are therefore closely linked with the preparation process for this catalyst. $Al_2O_3$ and $SiO_2$ may be used single or as a mixture of the both. From the $Al_2O_3$ and $SiO_2$, the $Al_2O_3$ is preferred. The special activation of aluminum hydroxide and/or aluminum oxide hydrate is preferred, respectively.

The invention therefore further relates to a process for the preparation of an $Al_2O_3$ and/or $SiO_2$ catalyst, which is specifically activated and promoted with halogen compounds, which is characterized in that aluminum hydroxide and/or aluminum oxide hydrate and/or silica gel is treated with excess solution of volatile ammonium salts, in order to absorb these salts, and the aluminum hydroxide and/or aluminum oxide hydrate and/or silica gel thus treated is separated from the remaining solution of these salts, is dried at 60° to 200° C. and is calcined at 400° to 800° C., with expulsion of the volatile ammonium salts and with formation of $Al_2O_3$ and/or $SiO_2$, and is thereafter promoted with 0.1 to 20% by weight, relative to the quantity of the $Al_2O_3$ and/or $SiO_2$, of at least one halogen compound of an element of the third to fifth main groups and second to eighth sub-groups of the periodic system (Mendeleev) and/or a hydrohalic acid.

In this context, a salt of ammonia or of a lower primary, secondary or tertiary aliphatic amine, such as methylamine, dimethylamine, trimethylamine, ethylamine, diethylamine or triethylamine, may be mentioned as an example of a volatile ammonium salt. Salts of ammonia are preferably employed. Inorganic or organic anions, such as fluoride, chloride, bromide, iodide, nitrate, sulphate, phosphate, carbonate, bicarbonate, bisulphate, hydrogen phosphate, acetate, propionate, formate, oxalate or benzoate, may be mentioned as anions. Salts of inorganic acids are preferred, and salts of the more readily volatile inorganic acids, such as the fluoride, chloride, bromide, iodide or nitrate, are particularly preferred. Ammonium nitrate is employed in a very particularly preferred manner.

Such a volatile ammonium salt, for example in an approximately 5 to 20% strength solution in a suitable solvent, such as water, methanol or ethanol, preferably water, is added to the aluminum hydroxide and/or aluminum oxide hydrate and/or silica gel, and is brought into contact with it for about half an hour to 6 hours, whilst stirring, in order to make the absorption by the aluminum compound and/or the silica gel as complete as possible. The absorptively bonded quantity of ammonium salt is about 10 to 70% by weight, relative to the dried aluminum hydroxide and/or aluminum oxide hydrate and/or silica gel.

Subsequently to this process, the aluminum hydroxide and/or aluminum oxide hydrate and/or silica gel with the absorptively bonded ammonium salt is separated from the excess solution, for example by filtration or centrifuging, and is dried at a temperature of from 60° to 200° C., preferably 100° to 160° C., if necessary in vacuo. The dried material is then subsequently calcined at 400° to 800° C., preferably 500° to 650° C., with expulsion of the volatile ammonium salts and with formation of the $Al_2O_3$ and/or $SiO_2$. The drying and the calcination can expediently be carried out in a forced-air oven, which can be charged with air as well as with nitrogen, argon or $CO_2$.

In a particular variant of the process, in the case that the compound to be promoted and to be specially activated to yield the catalyst is $Al_2O_3$, the starting material is not a separately prepared aluminum hydroxide and/or aluminum oxide hydrate, but a freshly precipitated aluminum hydroxide. In this process, a separately added salt is not used as the ammonium salt, but that salt is taken which is formed from the aqueous ammonia used as the precipitating agent and the anion of the aluminum salt employed. For example, aluminum chloride, aluminum bromide or aluminum nitrate is precipitated with concentrated or dilute aqueous ammonia at 0° to 90° C., preferably at room temperature, and the aluminum hydroxide formed thereby is left in contact with the precipitating solution, which contains the ammonium chloride, ammonium bromide or ammonium nitrate formed, for some time further, for example 0.5 to 6 hours. In the process, the aluminum hydroxide absorptively binds this ammonium salt which is present, and the aluminum hydroxide is then filtered off or separated off by centrifuging and is immediately subjected, without a washing operation, to the drying described above and then to the calcination.

The $Al_2O_3$ and/or $SiO_2$ formed by the simultaneous calcination and expulsion of the volatile ammonium salts is then present in a particularly active form, which can then be promoted with the abovementioned quantities of the halogen compounds described. For this purpose, the $Al_2O_3$ and/or $SiO_2$, brought to a particle size of 0.01 to 20 mm diameter, is brought into contact with the halogen compound, which is dissolved in a suitable solvent, and is then again calcined. In the great majority of cases, water is suitable as a solvent for the halogen compounds and/or hydrohalic acids described. In the case in which halogen compounds which are sensitive to hydrolysis are to be employed, an addition of the corresponding hydrohalic acid to the water can be undertaken to suppress this hydrolysis. Furthermore, in the case of water-sensitive halogen compounds, a polar solvent, such as acetone or acetonitrile, can be used. For the uniform promotion of the $Al_2O_3$ and/or $SiO_2$, it is expedient to use a volume of the solution of the solvent and the halogen compound described which approximately corresponds to the pore volume of the $Al_2O_3$ and/or $SiO_2$ determined according to a suitable method. For this purpose, a quantity of from 80 to 300, preferably 100 to 200, % by volume of solution, relative to the pore volume of the $Al_2O_3$ and/or $SiO_2$, may be mentioned as an example.

The promoted catalyst is then calcined for about 1 to 10, preferably 2 to 8 hours, at about 400° to 600° C., preferably 420° to 500° C. It is then ground to a particle size of from 0.05 to 10 mm, and is thereafter ready for use.

It has been found that the promoted $Al_2O_3$ and/or $SiO_2$ catalyst can be regenerated to its original activity after a relatively long period of use and/or declining activity of conversion by heating at 400° to 800° C., preferably 550° to 650° C. This regeneration can be effected in an $O_2$-containing atmosphere which can also contain, in addition to oxygen, inert gases, such as nitrogen or steam, or other gases, such as noble gases, CO or $CO_2$, with the addition of halogenated hydrocarbons, such as carbon tetrachloride, chloroform, chlorinated ethanes, dichloropropane, fluorochloroethane and the like. The pressure in the regeneration reactor is not important for the invention and can vary within wide limits, for example from 0.5 to 20 bar, preferably from 1 to 10 bar and particularly preferably from 2 to 5 bar. The catalyst to be regenerated is left under these conditions for 0.01 to 10, preferably 0.1 to 5 and particularly preferably 0.2 to 3 hours. The stated halogenated hydrocarbons are employed in an amount of, for example, 0.1 to 1% when the regeneration process is conducted discontinuouly and in an amount of 1 to 100 ppm, when the regeneration process is conducted continuously, these amounts being based on the total starting mixture, consisting of catalyst and the regeneration atmosphere.

The ratio of the catalyst to be regenerated to the stated medium representing the regeneration atmosphere can vary within wide limits. 200 to 5000 liters of this atmosphere per kilogram of the catalyst to be regenerated may for example be mentioned for the regeneration. The oxygen content of the regeneration atmosphere is for example 5 to 50% by volume of $O_2$; preferably air is used.

It can be expedient once again to carry out a promotion with halogen compounds, as explained above, before the regeneration step. However, this repeated promotion is not necessary in many cases.

The regenerated catalyst is then again able to be used fully effectively for the isomerization reaction. In the process according to the invention the catalyst can be used both in a fixed bed and in a mobilized catalyst bed whereby the mobilized bed is understood to be the contrast to a fixed bed arrangement and means any form of catalyst bed wherein the catalyst is moved by the gas feed. The turbulent bed or the fluidized bed may be mentioned as an example of the mobilized catalyst bed. The catalyst is preferably used in a mobilized catalyst bed, particularly preferably in a fluidized bed.

DESCRIPTION OF SPECIFIC EMBODIMENT

Figure 1:
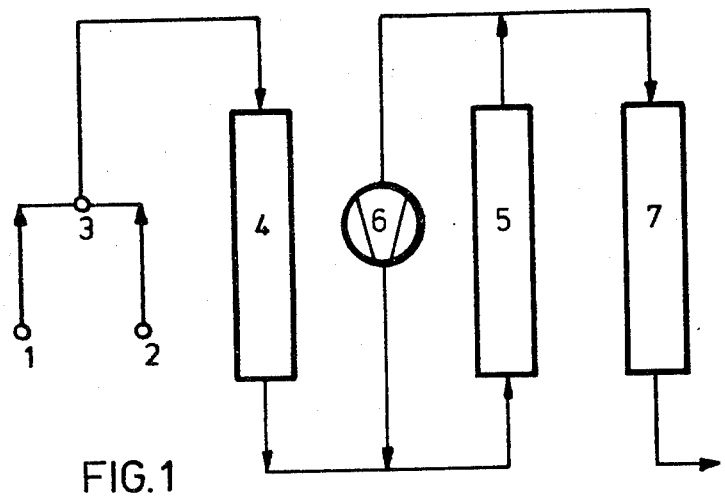
Figure 2:
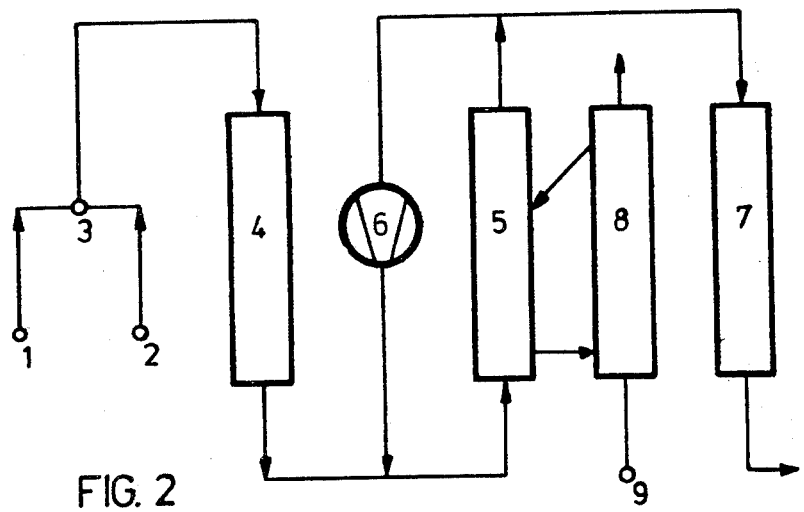

Referring to the drawings herein:

FIG. 1 represents a schematic flow diagram for carrying out an embodiment of the process of the invention; and FIG. 2 is another schematic flow diagram, similar to FIG. 1, showing another embodiment of the process of the invention.

A scheme for the operation of the process according to the invention is for example given in FIG. 1 wherein 1 denotes the input of the hydrocarbon stream containing n-alkene, 2 denotes the input of hydrogen, 3 denotes a mixing and metering device, 4 denotes a pre-heater, 5 denotes the reactor with the catalyst to be employed according to the invention. This catalyst can be arranged in the reactor as a fixed bed and also as a mobilized bed, preferably as a mobilized bed. In the FIG. 6 denotes a circulation pump through which a part of the reaction product removed at the head of 5 is again recycled into the lower part of reactor 5, and 7 denotes a cooler for the hot reaction products, which are then led away for further working up or processing.

It is known that many reactions in a fixed bed result in a high yield and good selectivity. In order to allow the reaction of n-alkenes into isoalkenes, especially n-butenes into isobutene, to proceed at an adequate speed the isomerization must be conducted at a high temperature, for example between 400° and 600° C., and at low pressures. As a result of the selected reaction conditions the yield, for example of isobutene, from this isomerization process is limited thermodynamically, so that the processes known in the literature are aimed at obtaining as high as possible a yield and selectivity especially by using the fixed bed. In doing so the above described disadvantages, i.e. the rapid loss in activity and selectivity of the catalyst caused by the undesired carbonization reaction, the formation of oligomers and cracking reactions, are consciously tolerated.

A further disadvantage for industrial application of isomerization in a fixed bed reaction is the continuously changing composition of the product and the necessary switching from one catalyst bed to the next to make a regeneration period possible.

It is therefore particularly advantageous that, using the above described catalyst, the skeleton isomerization of n-alkenes into isoalkenes can be achieved with a high yield and excellent selectivity without the mentioned disadvantages when the isomerization is conducted in a mobilized catalyst bed. In the use of this method one process variant, in which the catalyst is partly or completely replaced by fresh and/or regenerated catalyst, without interruption of the process, is particularly advantageous. For this purpose, the catalyst present in the process is removed from the reactor in an amount equivalent to the amount of fresh and/or regenerated catalyst introduced into the reactor. The removal of the catalyst present in the process and the replacement with fresh and/or regenerated catalyst can be continued intermittently or continuously. In intermittent removal and replacement of the catalyst the catalyst present in the process can, for example, be removed from the reactor completely or partly while being at the same time replaced by fresh catalyst, after which the isomerization reaction can then be continued without exchange of catalyst, until, after an appropriate period of time, the removal and replacement of the catalyst is repeated. Operation of the process using continuous removal and replacement of the catalyst is preferred. In general a procedure can be followed whereby the total amount of catalyst has been completely exchanged and replaced one, within a period of 5 days to up to 30 days, preferably 7 to 20 days, from the catalyst bed, either discontinuously or continuously. In continuous exchange and replacement this corresponds for example, to approximately 1 to 0.01% of the total amount of the catalyst load per hour.

The regeneration process itself can be carried out both discontinuously and continuously. A preferred embodiment is the combination of the continuous removal and replacement of the catalyst from the mobilized catalyst bed with a continuous regeneration of this catalyst in a special regeneration reactor separated from the isomerization reaction.

Of course, it is possible according to the invention to introduce into the mobilized catalyst bed of the isomerization reaction completely fresh catalyst instead of the removed catalyst. In a preferred manner, however, the regenerated catalyst is reintroduced. Fresh catalyst is in general only necessary in order to replace small losses of catalyst, for example, in the form of flue dust.

The use in the process according to the invention of the mobilized catalyst bed and the catalyst regeneration which is able to be carried out separately without interrupting the process, makes it possible to produce, for an unlimited period of operation and while regulating the amount of catalyst removed for regeneration, or reintroduced after regeneration, a reaction product of uniform composition with a uniform yield of isoalkene and under constant process conditions. It is therefore not necessary to tolerate, as in the prior art, a changing product composition and the switching on and off of various reaction systems. For example, in a fixed bed process, in order to be able to achieve a result anywhere near comparable to that of the turbulent bed process, one would have to burn off the carbonized catalyst and regenerate it after such short periods as after 12 to 24 hours at a time. Apart from the problems of changes and interruptions in the running of the process and the varying product composition resulting from this, any kind of burning off of coke on the catalyst means deterioration of the catalyst, and when burning off takes place frequently it has a negative affect on the activity and life time of the catalyst. It is furthermore possible according to the invention, while constantly carrying on the isomerization process, to replace catalysts with others, to promote them, regenerate them and to replace quantities of catalyst destroyed by abrasion or to compensate for losses in activity by introducing fresh catalyst. All the described operations with the catalyst take place outside the isomerization reactor and do not therefore cause contamination of the substances to be isomerised.

FIG. 2 shows another embodiment of the isomerization reaction with use of the catalyst in a mobilized catalyst bed and with continuous regeneration of the catalyst. In this Figures reference numbers (1) to (7) have the same meaning as in FIG. 1. In addition (8) denotes a regenerating reactor and (9) denotes the introduction of the substances required for the regenerating atmosphere which are described above.

FIG. 2 shows an example for carrying out the process according to the invention, when in the preferred manner catalyst is continuously removed from the mobilized catalyst bed in reactor (5), is continuously fed into the regenerating reactor (8) and is continuously passed from this regeneration reactor back into the mobilized catalyst bed in reactor (5).

In contrast to formerly described attempts at the skeleton isomerization of olefins, the process according to the invention can be carried out with high activity and high selectivity, without coke deposition, to give high yields of isoalkene, with a long life time of the catalyst. The long life time of the catalyst can be further improved by the regneration measures described, so that the process according to the invention can also be carried out extremely economically. It is surprising that the presence of volatile ammonium salts at the beginning of the calcination of the as yet unpromoted aluminum hydroxide and/or aluminum oxide hydrate and/or silica gel, which are expelled during the formation of the $Al_2O_3$ and/or $SiO_2$, impart such advantageous properties to the $Al_2O_3$ and/or $SiO_2$, that the remaining measures according to the invention, such as the promotion and the admixing of hydrogen with the starting products containing at least one n-alkene, develop their full effectiveness.

EXAMPLE 1

100 g of $Al(NO_3)_3.9H_2O$ are dissolved in 500 ml of distilled water, and the solution is precipitated with 60 ml of concentrated aqueous ammonia in the course of 2 hours. The precipitated aluminum hydroxide is stirred for a further 2 hours, and is filtered off and dried for 24 hours at 150° C. The dry mass is then heated for 1 hour under nitrogen at 600° C. A solution of 0.75 g of $SbF_3$ in 10 ml of distilled water is applied onto this $Al_2O_3$ carrier thus prepared, and the $Al_2O_3$ is dried for 2 hours at 150° C. and then calcined at 450° C. for 4 to 5 hours. The catalyst thus prepared is thereafter brought to the necessary particle size by crushing and fractional sieving.

EXAMPLE 2

To carry out this process, the apparatus schematically represented in FIG. 1 is used. Via the dosing device (3), a gaseous mixture of but-1-ene (1) and hydrogen (2) in the ratio by volume of 1:1.5 is conducted, via the pre-heater (4) into the reactor (5). A part of the reaction product is recycled into the reactor (5) via the circulation gas pump (6), in such an amount that the ratio by volume between input amount and amount of gas circulating is 1:1.

An aluminum oxide prepared according to Example 1, but promoted with 9.1% by weight of BiOCl, was employed as the catalyst. The reaction temperature was 480° C., the pressure 1 bar, and the gas velocity GHSV (gas hourly space velocity) 1,500 h$^{-1}$, corresponding to an average residence time of 2.4 seconds. The liquid reaction product removed beyond the cooler (7) had the following composition:

| | |
|---|---|
| C$_3$-hydrocarbon | 1.6% by weight |
| isobutene | 33.0% by weight |
| n-butenes | 50.6% by weight |
| butane, isobutane | 3.7% by weight |
| C$_5$- and higher hydrocarbons | 11.1% by weight |
| | 100.0% by weight. |

EXAMPLE 3

Corresponding to Example 2, a gaseous mixture of a hydrocarbon stream (1), consisting of 0.5% by weight of isobutene, 76% by weight of n-butenes and 23.5% by weight of butanes, and hydrogen (2) in the ratio by volume of 1:1.5 is conducted via the pre-heater (4) into the reactor (5), in an apparatus according to FIG. 1. An aluminum oxide prepared according to Example 1, but promoted with 1.5% by weight of BF$_3$, was employed as the catalyst. The circulation ratio was 1:1, the reaction temperature 450° C. and the gas velocity GHSV 1,500 h$^{-1}$, corresponding to an average residence time of 2.4 seconds. The liquid reaction product removed from beyond the cooler (7) has the following composition:

| | |
|---|---|
| C$_3$-hydrocarbons | 1.7% by weight |
| isobutene | 23.1% by weight |
| n-butenes | 38.6% by weight |
| butane, isobutane | 25.2% by weight |
| C$_5$- and higher hydrocarbons | 11.4% by weight |
| | 100.0% by weight |

EXAMPLES 4–6

A commercially available Filtrol Grade 13, corresponding to U.S. Pat. No. 3,663,453, and an Al$_2$O$_3$ prepared according to Example 1 were brought to the same particle size by crushing and sieving, and were promoted with 9.1% by weight of ZrOCl$_2$.8H$_2$O and employed as the catalyst. Furthermore, an Al$_2$O$_3$ according to Example 1, but without promotion, was included for comparison.

Corresponding to Example 2, a gaseous C$_4$-stream and hydrogen in the ratio of 1:1.5 was conducted via the pre-heater into the reactor. The ratio of circulating gas to input material was 1:1, the reaction temperature 480° C. and the gas velocity GHSV 1,500 h$^{-1}$, corresponding to an average residence time of 2.4 seconds. The liquid reaction product removed from beyond the cooler had the following composition:

| | Examples | | |
|---|---|---|---|
| | 4 | 5 | 6 |
| Catalyst | Filtrol Grade 13 + ZrOCl$_2$ according to U.S. Pat. No. 3,663,453 | Al$_2$O$_3$ according to Example 1 without doping | Al$_2$O$_3$ + ZrOCl$_2$ corresponding to Example 1 |
| C$_3$ | 1.2 | 0.6 | 2.0 |
| n-butane/isobutane | 23.6 | 22.5 | 26.2 |
| isobutene | 9.8 | 12.4 | 24.2 |
| but-1-ene | | | |
| but-2-ene | 61.6 | 62.3 | 39.7 |
| C$_5$ and higher | 3.8 | 2.2 | 7.9 |
| conversion | 18.0 | 17.0 | 47.1 |
| selectivity | 52.2 | 75.4 | 60.6 |

The catalyst in Experiment 4 coked after about 1 hour and showed therewith a strong decline in activity and a great deterioration of the initial isobutene value, whilst Experiment 6 was terminated after 72 hours without detectable change of the values for activity and yield.

EXAMPLE 7

Corresponding to Examples 2 and 3, a gaseous mixture of a hydrocarbon stream (1), consisting of 1% by weight of isobutene, 75% by weight of n-butene and 24% by weight of butanes, and hydrogen (2) in the ratio by volume of 1:1.5 is conducted via the preheater (4) into the reactor (5), in an apparatus according to Example 1, but promoted with 15% by weight of hydrogen chloride, was employed as the catalyst. The circulation ratio was 1:1, the reaction temperature 450° C. and the gas velocity GHSV 1,500 h$^{-1}$, corresponding to an average residence time of 2.4 seconds. The liquid reaction product removed from beyond the cooler (7) has the following composition:

| | |
|---|---|
| C$_3$-hydrocarbons | 1.9% by weight |
| isobutene | 25.1% by weight |
| n-butenes | 41.3% by weight |
| butane, isobutane | 23.6% by weight |
| C$_5$- and higher hydrocarbons | 8.1% by weight |
| | 100.0% by weight |

EXAMPLE 8 (FOR COMPARISON)

A gaseous mixture consisting of a hydrocarbon stream (1) consisting of 0.5% by weight of isobutene, 71% by weight of n-butenes, 28% by weight of butanes and 0.5% by weight of other constituents, is mixed with hydrogen (2) in an apparatus as in FIG. 1 in a volume ratio of 1:1.5 and is passed via the pre-heater (4) into the fixed bed reactor (5). The reaction temperature is 450° C., the GHSV 1,500 h$^{-1}$ and the circulation ratio 1:1 (volume/volume).

The liquid reaction product removed from beyond the cooler (7) has the following compositions during the course of the reaction time:

TABLE 1

| | (Example 8) | | | |
|---|---|---|---|---|
| | Reaction time in h | | | |
| Components in % by weight | after 10 h | after 20 h | after 45 h | regenerated after 50 h |
| C$_3$-hydrocarbon | 1.5 | 1.3 | 0.8 | 0.8 |
| isobutene | 25.1 | 23.5 | 19.0 | 21.5 |
| n-butene | 39.7 | 43.6 | 49.1 | 45.0 |
| butane, isobutane | 28.9 | 27.7 | 27.9 | 28.9 |
| C$_5$-hydrocarbons and higher hydrocarbons | 4.8 | 3.9 | 3.2 | 3.8 |
| total | 100.0 | 100.0 | 100.0 | 100.0 |

EXAMPLE 9

In an apparatus as in FIG. 2, in which the catalyst prepared in accordance with Example 1 was arranged in a fluidized layer in reactor (5), a hydrocarbon stream (1), consisting of a mixture of 0.5% by weight of isobutene, 76% by weight of n-butenes and 23.5% by weight of butanes is reacted with a hydrogen stream (2) in a ratio of 1:1.5. The circulation ratio of the discharged and reintroduced amount of reaction gas is 1:1, the reaction temperature is 450° C. and the gas velocity GHSV is 1,500 h$^{-1}$. The catalyst is removed from the reactor (5) and continuously regenerated with air (9) in the reactor (8) and reintroduced into the fluidized bed reactor (5). The reaction product removed from beyond the cooler (7) had the following composition during the course of the reaction time:

TABLE II (Example 9)

| Components in % by weight | Reaction time in h | | | |
|---|---|---|---|---|
| | after 20 h | after 45 h | after 85 h | after 100 h |
| $C_3$-hydrocarbon | 1.1 | 1.4 | 1.2 | 0.8 |
| isobutene | 25.6 | 25.4 | 25.3 | 25.0 |
| n-butene | 39.0 | 40.4 | 41.6 | 41.5 |
| butane, isobutane | 26.0 | 25.8 | 25.5 | 25.0 |
| $C_5$hydrocarbons and higher hydrocarbons | 8.3 | 7.0 | 6.4 | 7.7 |
| total | 100.0 | 100.0 | 100.0 | 100.0 |

What is claimed is:

1. A catalyst comprising an $Al_2O_3$ and/or $SiO_2$ containing 0.1 to 20% by weight, relative to the quantity of $Al_2O_3$ and/or $SiO_2$, of at least one halogen compound of an element of the third to fifth main groups and/or second to eighth sub-groups of the Mendeleen periodic system and/or a hydrogen halide acid which catalyst has been prepared by a process comprising:
   (a) calcining an aluminum hydroxide and/or aluminum oxide hydrate and/or silica gel having a content of about 10–70% by weight relative to dried aluminum hydroxide and/or aluminum oxide hydrate and/or silica gel of volatile ammonium salts absorptively bonded whereby to provide $Al_2O_3$ and/or $SiO_2$ by expulsion of the volatile ammonium salts;
   (b) contacting the resultant $Al_2O_3$ and/or $SiO_2$ with a halogen compound of an element of the third to fifth main groups and/or second to eighth sub-groups of the periodic system and/or a hydrogen halide acid.

2. A catalyst according to claim 1, wherein after contact of said $Al_2O_3$ and/or $SiO_2$ with said halogen compound or hydrogen halide acid the $Al_2O_3$ and/or $SiO_2$-containing catalyst is calcined.

3. A catalyst according to claim 2, wherein the calcination is carried out for between one and 10 hours at a temperature of 400° to 600° C.

4. A catalyst according to claim 3, which has a particle size of 0.05 to 10 mm.

5. A catalyst according to claim 1 wherein said resultant $Al_2O_3$ and/or $SiO_2$ is treated with a halogen compound of aluminum, boron, tin, germanium, titanium, arsenic, antimony, bismuth, zinc, cadmium, lanthanum, vanadium, tungsten, iron, cobalt, or nickel or a hydrogen halide acid.

6. A catalyst according to claim 5 prepared by a process wherein aluminum hydroxide, aluminum oxide hydrate and/or silica gel is treated with a salt of ammonia or a lower primary, secondary or tertiary aliphatic amine and is thereafter, without a washing step, dried and calcined according to Step a.

7. A catalyst according to claim 6 wherein said salt of ammonia, or of a lower primary, secondary or tertiary aliphatic amine is methyl amine, dimethyl amine, trimethyl amine, ethyl amine, diethyl amine, triethyl amine, or a fluoride, chloride, bromide, iodide, nitrate, sulphate, phosphate, carbonate, bicarbonate, bisulphate, hydrogen phosphate, acetate, propionate, formate, oxalate, or benzoate of ammonium.

8. A process for the preparation of an $Al_2O_3$ and/or $SiO_2$ catalyst which comprises:
   (a) contacting an aluminum hydroxide and/or aluminum oxide hydrate and/or silica gel with an excess solution of a volatile ammonium salt to absorb said salt in an amount of about 10–70% by weight relative to dried aluminum hydroxide and/or aluminum oxide hydrate and/or silica gel on said aluminum hydroxide, aluminum oxide hydrate or silica gel;
   (b) drying the so-treated aluminum hydroxide, aluminum oxide hydrate or silica gel at a temperature of 60° to 200° C.;
   (c) calcining the so-dried material at a temperature of 400° to 800° C. with expulsion of the volatile ammonium salts whereby to form $Al_2O_3$ and/or $SiO_2$;
   (d) contacting said $Al_2O_3$ and/or $SiO_2$ with at least one halogen compound of an element of the third to fifth main group and/or second to eighth sub-group of the periodic system, or a hydrogen halide acid.

9. A process according to claim 8, wherein thereafter the $Al_2O_3$ and/or $SiO_2$ is calcined at a temperature of 400° to 600° C. for 1 to 10 hours.

10. A process according to claim 8, wherein said $Al_2O_3$ and/or $SiO_2$ is contacted with a halogen compound of the third to fifth main group and/or second to eighth sub-group of the periodic system.

11. A process according to claim 8, wherein said $Al_2O_3$ and/or $SiO_2$ is contacted with a hydrogen halide acid.

12. A process according to claim 10, wherein said halogen compound is a chloride, fluoride or bromide of aluminum, boron, titanium, germanium, tin, arsenic, antimony, bismuth, zinc, cadmium, lanthanum, vanadium, tungsten, iron, cobalt or nickel.

13. A process according to claim 8, wherein said volatile ammonium salt is a salt of ammonia or of a lower primary, secondary or tertiary aliphatic amine.

14. A process according to claim 13, wherein said salt is a salt of methyl amine, dimethyl amine, trimethyl amine, ethyl amine, diethyl amine or triethyl amine.

15. A process according to claim 13, wherein said salt is ammonium fluoride, ammonium chloride, ammonium bromide, ammonium iodide, ammonium nitrate, ammonium sulfate, ammonium phosphate, ammonium carbonate, ammonium bicarbonate, ammonium bisulphate, ammonium hydrogen phosphate, ammonium acetate, ammonium propionate, ammonium formate, ammonium oxalate or ammonium benzoate.

16. A process according to claim 15, wherein said halogen compound is BiOCl.

17. A process according to claim 15, wherein said halogen compound is $BF_3$.

18. A process according to claim 15, wherein said halogen compound is $ZrOCl_2.H_2O$.

19. A process according to claim 8 wherein the drying and calcining of Steps b and c are effective without a washing operation.

* * * * *